United States Patent [19]

Tashiro et al.

[11] 4,107,203

[45] Aug. 15, 1978

[54] OPTICAL RESOLUTION OF DL-α-PHENYLGLYCINE HYDROCHLORIDE

[75] Inventors: Yasuhisa Tashiro, Yokohama; Hideo Sugimura, Tokyo; Toshiaki Arai, Washinomiya; Masao Suzuki, Tokyo; Tadashi Shirai, Musashino, all of Japan

[73] Assignee: Nippon Kayaku Kabushiki Kaisha, Tokyo, Japan

[21] Appl. No.: 822,826

[22] Filed: Aug. 8, 1977

Related U.S. Application Data

[63] Continuation of Ser. No. 657,532, Feb. 12, 1976, abandoned.

[30] Foreign Application Priority Data

Feb. 25, 1975 [JP] Japan ................................. 50-23072

[51] Int. Cl.$^2$ .......................................... C07C 101/04
[52] U.S. Cl. ................................................. 260/518 R
[58] Field of Search .................................... 260/518 R

[56] References Cited

U.S. PATENT DOCUMENTS

| 3,381,031 | 4/1968 | Dwyer et al. ................... 260/518 R |
| 3,933,902 | 1/1976 | Watanabe et al. .............. 260/518 R |

FOREIGN PATENT DOCUMENTS 1,210,495  10/1970  United Kingdom .................... 260/518

OTHER PUBLICATIONS

Chibata et al, Chem. Abst., vol. 83, #10843e (1975).
Nakamura et al, Chem. Abst., vol. 76, #14923j (1972).
Kamata et al, Chem Abst. vol. 78, #148236n (1973).

Primary Examiner—James O. Thomas, Jr.
Assistant Examiner—James H. Reamer
Attorney, Agent, or Firm—Lane, Aitken, Dunner & Ziems

[57] ABSTRACT

In order to separate optically active D- or L-α-phenylglycine hydrochloride from a supersaturated solution of DL-α-phenylglycine hydrochloride seed crystals of the desired D- or L-isomer are added to the solution in the presence of a metal chloride.

6 Claims, No Drawings

OPTICAL RESOLUTION OF DL-α-PHENYLGLYCINE HYDROCHLORIDE

This is a continuation of application Ser. No. 657,532 filed Feb. 12, 1976, now abandoned.

BACKGROUND OF THE INVENTION

The present invention relates to a novel process for the separation of optically active D- or L-α-phenylglycine hydrochloride from a supersaturated solution of DL-α-phenylglycine hydrochloride by direct optical resolution.

In the optical resolution of DL-α-phenylglycine for many years it has been commercial practice to form diastereomers with d-camphor-sulfonic acid. Further, in fractional crystallization it is known to form ammonium salts (Japanese Patent Publication No. 45,383/74) or monoethylamine salts (Japanese Patent Laid-Open Application No. 29,715/73) of N-acetyl-α-phenylglycine. These prior art methods, however, have serious drawbacks in that the commercial method employs d-camphor which is an expensive natural substance, while the latter methods take a complicated route, that is, an α-phenylglycine racemate is converted into an acetyl derivative which is resolved into two isomers, each of which must, in turn, be subjected to hydrolysis of the acetyl groups.

In general, when an α-amino acid is to be optically resolved by fractional crystallization, it is, of course, advantageous to treat the amino acid as directly as possible. However, attempts to selectively crystallize isomers of an amino acid in the form of the free amino acid, simple salts of a mineral acid or metal salts have rarely met with success. Japanese Patent Laid-Open Application No. 14,645/70 discloses the purification of a salt of optically active α-phenylglycine with a mineral acid on the basis of the differing solubilities of salts of the mineral acid the optically active isomer and a DL-mixture (a racemate). Since this publication discloses that the resulting mineral acid salt of α-phenylglycine is still a racemic compound, this method does not lead to resolution by fractional crystallization, but to only purification.

lycine hydrochloride and the metal chloride without adversely affecting effective resolution.

While the separation of the present invention provides a crude product of optically active α-phenylglycine hydrochloride which contains some amounts of the metal chloride, the crude product has been identified as α-phenylglycine hydrochloride by ultraviolet spectra, infrared spectra and the like. A desirable pure product of optically active α-phenylglycine hydrochloride can be obtained in any suitable manner, for example, by dissolving the crude product in an aqueous solution containing hydrochloric acid in a suitable concentration and recrystallizing from this solution.

The metal chloride used herein must have the characteristics that it can provide the racemate with a solubility larger than or substantially equal to those of the optically active isomers and render the supersaturated condition of the racemate sufficiently stable to selectively crystallize the optically active isomer. Although the prior resolution practice requires that an optically active isomer be insoluble in a saturated solution of the racemate, the process of the present invention does not necessarily have this requirement. It is believed that both the solubility of the racemate and the optically active isomer and the stability of the supersaturation of the racemate are more important factors in the present process.

According to the present invention there is provided a process for separating optically active D- or L-α-phenylglycine hydrochloride from a supersaturated solution of DL-α-phenylglycine hydrochloride which comprises adding seed crystals of D- or L-α-phenylglycine hydrochloride to the supersaturated solution in the presence of at least one metal chloride to selectively induce the crystallizaton of the corresponding optically active D- or L-α-phenylglycine hydrochloride. When the supersaturated solution contains substantially equal amounts of D- and L-α-phenylglycine hydrochlorides the seed crystals may consist of either D- or L-isomer. On the other hand, when the supersaturated solution contains in excess either D- or L-α-phenylglycine hydrochlorides the seed crystals should be of the same isomer as that contained in excess.

Values of the solubility of α-phenylglycine hydro-

Table-1

| Crystal of metal chloride Mol/1000H$_2$O | CdCl$_2$ . H$_2$O | | FeCl$_3$ . H$_2$O | | SnCl$_4$ . 5H$_2$O | | SnCl$_2$ . 2H$_2$O | | ZnCl$_2$ | |
|---|---|---|---|---|---|---|---|---|---|---|
| | DL g/soln 100g | D g/soln 100g | DL g/soln 100g | D g/soln 100g | DL g/soln 100g | D g/soln 100g | DL g/soln 100g | D g/soln 100g | DL g/soln 100g | D g/soln 100g |
| 1.0 | 3.95 | 9.32 | 16.50 | 14.07 | 27.69 | 26.37 | 34.02 | 27.58 | 11.20 | 11.96 |
| 3.0 | 5.77 | 14.32 | 6.96 | 8.18 | 25.65 | 24.26 | 35.43 | 32.85 | 22.13 | 21.12 |
| 5.0 | 18.35 | 16.26 | 7.39 | 6.92 | 27.20 | 25.00 | 60.38 | 58.78 | 37.81 | 32.39 |
| 7.0 | 18.52 | 13.99 | 7.21 | 6.71 | 29.65 | 26.14 | 82.58 | 80.37 | 15.70 | 13.38 |

DESCRIPTION OF THE INVENTION

It has now been discovered that the solubility of α-phenylglycine hydrochloride is remarkably affected by the presence of a metal chloride. And that optically active α-phenylglycine hydrochloride can be separated by fractional crystallization of a supersaturated solution of DL-α-phenylglycine hydrochloride in the presence of one or more metal chlorides such as zinc chloride, stannous chloride, stannic chloride, cadmium chloride, ferric chloride and the like.

The solution used in the present invention may contain free hydrochloric acid in addition to the α-phenylgchloride in water at 30° C in the presence of various metal chlorides are shown in Table 1.

It is apparent from Table 1 that the concentration of the metal chloride in the solution may be varied depending on the type of metal chloride used. A preferred concentration may be more than 5 moles for cadmium chloride, 1 to 2 or more than 5 moles for ferric chloride, more than 1 mole for stannous and stannic chlorides, and 3 moles for zinc chloride per liter of water. The quantity of the seed crystals added may also be varied over a wide range. A preferred quantity is in the order of 0.1 to 5% by weight on the basis the solute. If either of optically active D- or L-α-phenylglycine hydrochloride is contained in excess, the seed crystals need not necessarily be added.

As a solvent water is preferred in practice, while water-soluble organic solvents such as aqueous methanol, aqueous ethanol, etc. may also be employed.

The temperature at which the resolution, i.e., the crystallization, is carried out may be in the range of 0° to 50° C, preferably 20° to 30° C.

After the precipitated crystals of optically active D- or L-α-phenylglycine hydrochloride are removed there is obtained a mother liquor which is richer in the other isomer. To this mother liquor is added DL-α-phenylglycine in a sufficient amount to yield a supersaturated solution. On the addition of seed crystals of the other optical active α-phenylglycine hydrochloride to this solution the corresponding isomer may be selectively crystallized.

As described in the foregoing, the present invention offers the advantages that α-phenylglycine can be directly subjected to optical resolution in the very simple form of a hydrochloride and that the crude crystals of optically active α-phenylglycine hydrochloride can be readily purified by recrystallization. The less desirable optically active α-phenylglycine hydrochloride, usually the L-isomer, may be readily converted into a racemate in a conventional manner so that it can be repeatedly used as a raw material for the resolution. This complete usage of the raw material represents a great commercial advantage.

According to the present invention there are obtained optically active D- and L-α-phenylglycine hydrochlorides. D-α-phenylglycine hydrochloride is useful as a raw material for the synthesis of semisynthetic penicillins and cephalosporins. For example, D-α-phenylglycine hydrochloride may be converted to D-α-phenylglycine chloride hydrochloride or neutralized with an alkali to free α-phenylglycine.

The present invention will now be illustrated by the following Examples.

EXAMPLE 1

To a mixture of 91.5 g of conc. hydrochloric acid and 21.5 g of water were added 54.5 g of zinc chloride, 130 g of DL-α-phenylglycine and 5 g of D-α-phenylglycine with heating at 75° C until dissolved. The resulting solution was cooled to 39° C and then seeded with 0.83 g of D-α-phenylglycine hydrochloride at the same temperature. With gentle stirring the solution was gradually cooled and then separated into solid and liquid phases, yielding 18.1 g of crude D-α-phenylglycine hydrochloride which had a specific rotation of $$[\alpha]_D^{20} = -90.5° \ (C = 1, \text{N HCl})$$

The thus obtained crude crystals were dissolved in 30.8 g of 2N hydrochloric acid solution with heating. Thereafter, the solution was cooled to 30° C and then the precipitated crystals were removed by filtration. There was obtained 11.8 g of D-α-phenylglycine hydrochloride which had a specific rotation of $$[\alpha]_D^{20} = -127.2° \ (C = 1, \text{N HCl})$$

EXAMPLE 2

To a mixture of 89.6 g of conc. hydrochloric acid and 26.6 g of water were added 126.4 g of stannous chloride dihydrate, 117.3 g of DL-α-phenylglycine and 3.6 g of D-α-phenylglycine with heating until dissolved. The resulting solution was cooled to 25° C and then seeded with 0.1 g of D-α-phenylglycine hydrochloride at this temperature. The solution was stirred at the same temperature for some period and then separated into solid and liquid phases, yielding 7.3 g of crude D-α-phenylglycine hydrochloride which had a specific rotation of $$[\alpha]_D^{20} = -101.9° \ (C = 1, \text{N HCl})$$

The crude crystals were purified in accordance with the procedure described in Example 1, yielding 5.5 g of D-α-phenylglycine hydrochloride which had a specific rotation of $$[\alpha]_D^{20} = -127.2° \ (C = 1, \text{N HCl})$$

EXAMPLE 3

To a mixture of 8.9 g of conc. hydrochloric acid and 72.5 g of water were added 140 g of stannic chloride (in the form of crystal), 104.5 g of DL-α-phenylglycine hydrochloride and 5.5 g of D-α-phenylglycine hydrochloride with heating until dissolved. The resulting solution was cooled to 25° C and then seeded with 0.1 g of D-α-phenylglycine hydrochloride. The solution was stirred at the same temperature for a period of time and then separated into solid and liquid phases, yielding 17.15 g of crude D-α-phenylglycine hydrochloride.

The crude crystals were purified in accordance with the procedure described in Example 1, yielding 10.52 g of D-α-phenylglycine hydrochloride which had a specific rotation of $$[\alpha]_D^{20} = 127.1° \ (C = 1, \text{N HCl})$$

EXAMPLE 4

To a mixture of 91.5 g of conc. hydrochloric acid and 21.5 g of water were added 54.5 g of zinc chloride and 135 g of DL-α-phenylglycine with heating at 75° C until dissolved. The resulting solution was cooled to 39° C and then seeded with 1.0 g of D-α-phenylglycine hydrochloride at that temperature. With gentle stirring the solution was gradually cooled and then separated into solid and liquid phases, yielding 9.1 g of crude D-α-phenylglycine hydrochloride which had a specific rotation of $$[\alpha]_D^{20} = -88.3° \ (C = 1, \text{N HCl})$$

The crude crystals were purified in accordance with the procedure described in Example 1, yielding 5.6 g of D-α-phenylglycine hydrochloride which had a specific rotation of
$$[\alpha]_D^{20} = -127.2° \ (C = 1, \text{N HCl})$$

EXAMPLE 5

To a mixture of 91.5 g of conc. hydrochloric acid and 21.5 g of water were added 54.5 g of zinc chloride and 135 g of DL-α-phenylglycine with heating at 75° C until dissolved. The resulting solution was cooled to 37° C and then seeded with 5.0 g of L-α-phenylglycine hydrochloride at that temperature. With gentle stirring the solution was gradually cooled and then separated into solid and liquid phases, yielding 13.2 of crude L-α-phenylglycine hydrochloride which had a specific rotation of $$[\alpha]_D^{20} = +99.4° \ (C = 1, \ N \ HCl)$$

The crude crystals were purified in accordance with the procedure described in Example 1, yielding 9.8 g of L-α-phenylglycine hydrochloride which had a specific rotation of $$[\alpha]_D^{20} = +127.2° \ (C = 1, \ N \ HCl)$$

What is claimed is:

1. A process for separating optically active D- or L-α-phenylglycine hydrochloride from a supersaturated aqueous solution of DL-α-phenylglycine hydrochloride which comprises adding seed crystals of D- or L-α-phenylglycine hydrochloride to said supersaturated solution in the presence of at least one metal chloride selected from the group consisting of zinc chloride, stannous chloride, stannic chloride, cadmium chloride and ferric chloride, and cooling to selectively induce crystallization of the corresponding optically active D- or L-α-phenylglycine hydrochloride and separating the crystals from the solution.

2. The process according to claim 1 wherein said supersaturated solution contains substantially equal amounts of D- and L-α-phenylglycine hydrochlorides and the seed crystals are the D- or L- isomer.

3. The process according to claim 1 wherein said supersaturated solution contains an excess of D- or L-α-phenylglycine hydrochloride and the seed crystals consist of the isomer contained in excess.

4. The process according to claim 1 wherein said seed crystals of an optically active isomer are added in an amount of 0.1 to 5% by weight based on the DL-α-phenylglycine hydrochloride in the supersaturated solution.

5. The process according to claim 1 wherein said seed crystals are D-α-phenylglycine hydrochloride.

6. The process according to claim 1 wherein said crystallization is conducted at a temperature of 10 to 50° C.

* * * * *

UNITED STATES PATENT AND TRADEMARK OFFICE
CERTIFICATE OF CORRECTION

PATENT NO. : 4,107,203

DATED : August 15, 1978

INVENTOR(S) : TASHIRO ET AL

It is certified that error appears in the above—identified patent and that said Letters Patent are hereby corrected as shown below:

Column 1, line 36, change "/70" to --/73--;
         line 38, delete "of salts";
         line 39, after "acid" insert --salts--.

Signed and Sealed this

Twenty-sixth Day of February 1980

[SEAL]

Attest:

SIDNEY A. DIAMOND

Attesting Officer      Commissioner of Patents and Trademarks